US008568438B2

(12) United States Patent  (10) Patent No.: US 8,568,438 B2
Burbank et al.  (45) Date of Patent: Oct. 29, 2013

(54) SLEEP APNEA THERAPY WITH NASO-PHYRANGEAL BYPASS

(75) Inventors: Fred Burbank, Laguna Nigel, CA (US); Mike Jones, San Clemente, CA (US); Al Memmolo, Carlsbad, CA (US)

(73) Assignee: Nasolex, San Clemente, CA (US)

( * ) Notice: Subject to any disclaimer, the term of this patent is extended or adjusted under 35 U.S.C. 154(b) by 567 days.

(21) Appl. No.: 12/725,875

(22) Filed: Mar. 17, 2010

(65) Prior Publication Data

US 2010/0242967 A1  Sep. 30, 2010

Related U.S. Application Data

(60) Provisional application No. 61/160,892, filed on Mar. 17, 2009.

(51) Int. Cl.
*A61M 29/00* (2006.01)
*A61M 15/08* (2006.01)

(52) U.S. Cl.
USPC ..................................... 606/196; 128/207.18

(58) Field of Classification Search
USPC .................. 604/506, 508, 509, 514, 516; 128/207.18; 606/196, 199
See application file for complete search history.

(56) References Cited

U.S. PATENT DOCUMENTS

| | | | |
|---|---|---|---|
| 4,819,619 A * | 4/1989 | Augustine et al. | 128/200.26 |
| 4,943,289 A * | 7/1990 | Goode et al. | 606/1 |
| 5,002,531 A | 3/1991 | Bonzel | |
| 5,181,911 A * | 1/1993 | Shturman | 604/103.07 |
| 5,183,085 A * | 2/1993 | Timmermans | 140/89 |
| 5,951,458 A * | 9/1999 | Hastings et al. | 600/3 |
| 6,183,493 B1 * | 2/2001 | Zammit | 606/196 |
| 6,394,093 B1 | 5/2002 | Lethi | |
| 7,100,612 B2 * | 9/2006 | Dunlap | 128/207.18 |
| 2001/0029388 A1 * | 10/2001 | Kieturakis et al. | 606/190 |
| 2004/0020492 A1 | 2/2004 | Dubrul et al. | |
| 2006/0205992 A1 * | 9/2006 | Lubock et al. | 600/3 |
| 2008/0053458 A1 * | 3/2008 | De Silva et al. | 128/207.18 |
| 2009/0266365 A1 * | 10/2009 | Oberle | 128/207.18 |

OTHER PUBLICATIONS

International Search Report and Written Opinion for PCT Patent App. No. PCT/US2010/027634 (May 12, 2010).

* cited by examiner

*Primary Examiner* — Theodore J Stigell
*Assistant Examiner* — Jenna Zhang
(74) *Attorney, Agent, or Firm* — Cermak Nakajima LLP; Adam J. Cermak

(57) ABSTRACT

Naso-pharyngeal devices for treating sleep apnea can perform two functions simultaneously: keeping an open airway through an inner lumen of the device; and support for the tissue in the airway, because keeping the tissue from completely collapsing creates the possibility of some air movement around the device in the critical areas associated with obstructive sleep apnea.

13 Claims, 5 Drawing Sheets

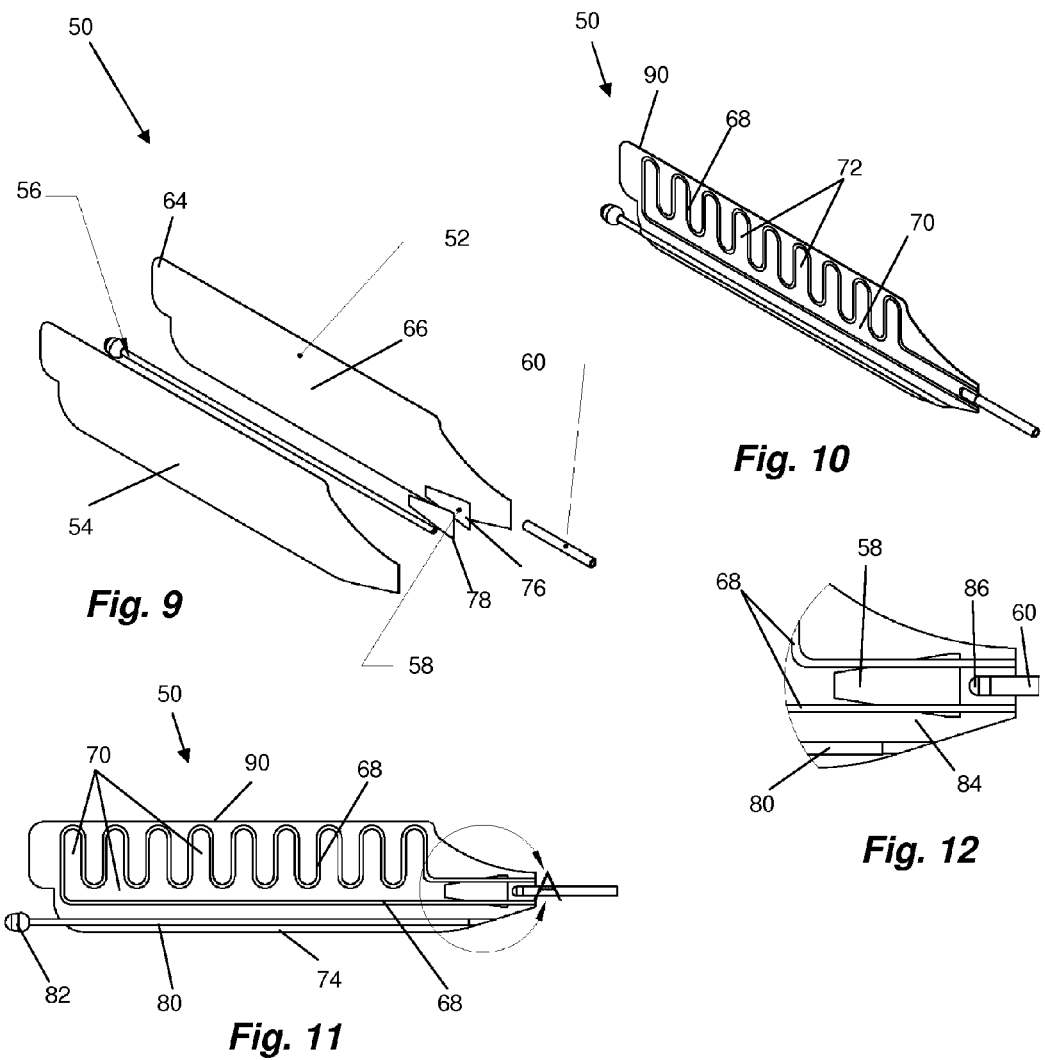

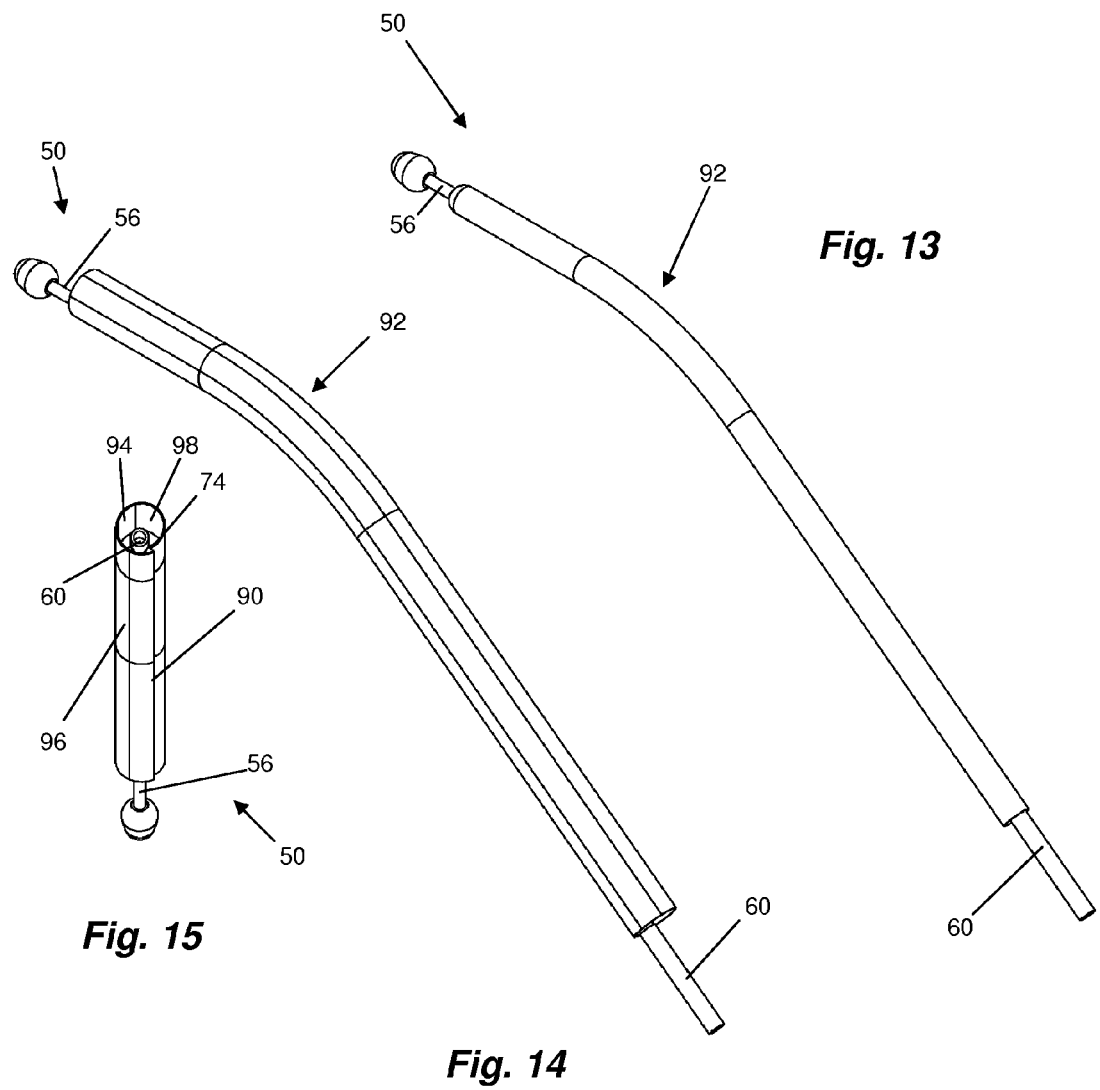

SLEEP APNEA THERAPY WITH NASO-PHYRANGEAL BYPASS

This application claims priority under 35 U.S.C. §119 to U.S. provisional application No. 61/160,892, filed 17 Mar. 2009, the entirety of which is incorporated by reference herein.

BACKGROUND

1. Field of Endeavor

The present invention relates to devices, systems, and processes useful for the treatment of apnea.

2. Brief Description of the Related Art

Breathing and Sleep

I. Breathing Background

Breathing consists of taking air into the lungs, or inhalation, and expelling air from the lungs, or expiration. Normally, inspiration is an active process requiring various muscles to contract while expiration is passive, a recoil from energy previously stored in muscles, ligaments, and tendons during inspiration.

Breathing is orchestrated by the brain which integrates emotional, chemical, and physical stimuli to regulate air movement into and out of the lungs. Regulation is controlled through the activation of motor nerves originating in the brain (cranial nerves or CN) and from nerves whose bodies are in the spinal cord. When recruited, these nerves cause various muscles to contract or to remain relaxed. In humans, quiet breathing occurs primarily through the cyclical stimulation of the muscles of the two hemi-diaphragms.

Breathing is under conscious and unconscious control. With an intact brain, an individual can take or not take a breath when ever desired. Singers and wind instrument musicians control breathing consciously to make music; swimmers gulp in a full lung of air in a second. Voluntary control of breathing originates in the cerebral cortex, although, in the extreme, various chemo-receptor reflexes are capable of overriding conscious control.

However, most of the time breathing is unconsciously controlled by specialized centers in the brainstem, which automatically regulate the rate and depth of breathing to match the body's needs at any given time. In addition to involuntary control of breathing by these respiratory brain centers, breathing is unconsciously influenced by a person's emotional state, by way of inputs from the limbic system, and by ambient temperature, by way of the hypothalamus.

Breathing rate and depth of breathing is tightly controlled by the brain. Changes in rate and depth of breathing are determined primarily by blood levels of carbon dioxide and secondarily by low or very low blood concentrations of oxygen. Chemo-receptors associated with three arteries, the carotid bodies at both carotid bifurcations and in the aortic arch, respond to changes in the blood concentration oxygen and carbon dioxide. Afferent neurons from the carotid bodies and aortic bodies reach the brain by way of the glossopharyngeal nerve (CN IX) and the vagus nerve (CN X), respectively.

Levels of $CO_2$ rise in the blood when the metabolic consumption of $O_2$ is increased beyond the capacity of the lungs to expel $CO_2$. $CO_2$ is stored in the blood primarily as bicarbonate ($HCO_3-$) ions, first by conversion to carbonic acid ($H_2CO_3$) through the enzyme carbonic anhydrase, and then by disassociation of this acid into H+ and $HCO_3-$. Build-up of $CO_2$ therefore causes an equivalent increase in hydrogen ion concentration. By definition, an increase in blood hydrogen ion concentration is a decrease in blood pH. A drop in blood pH stimulates the chemo-receptors in the medulla oblongata and the pons, in the brain.

When the brain senses that carbon dioxide concentration is high, that pH is low, and that oxygen concentration is low, it sends nerve impulses through the phrenic and thoracic nerves, respectively, to the muscles of the diaphragms and the intercostal muscles, through the hypoglossal nerve (CN XII) to the muscles of the tongue, and through the recurrent laryngeal nerve (a branch of CN X) to the muscles of the larynx. These and other nerve impulses cause the hemi-diaphragm muscle to contract, inhibits contraction of the intercostal muscles, and cause the complex muscles in the pharynx to contract. Contraction of the hemi-diaphragm muscles cause the volume to the thoracic cage to increase. Since the volume of the lungs does not instantly increase with a change in volume of the thorax, a transient drop in intra-thoracic (and intra-pleural and intra-esophageal) pressures occurs. Decreased intra-thoracic pressure causes the volume of the lungs to expand, which causes air to enter the nostrils and/or mouth, to flow through the nasopharynx and oropharynx, the laryngopharynx, the larynx, the trachea, the bronchi, and, finally, the alveoli.

Mouth breathing refers to the state of inhaling and exhaling primarily through the mouth. A healthy individual normally breathes through the nose while resting or doing light exercise, and breathes simultaneously through both the nose and mouth during vigorous aerobic exercise, in order to supply sufficient oxygen for metabolic needs. Excessive mouth breathing causes problems because air is not filtered and warmed as much as when it is inhaled through the nose, as it bypasses the nasal canal and paranasal sinuses, and dries out the mouth. Mouth breathing is often associated with congestion, obstruction, or other abnormalities of the nasal passage ways. Everyone mouth breathes when the nose is stopped up by a cold. Mouth breathing is associated with obstructive sleep apnea.

The phayrnx is a complex fibromuscular tube which extends from the base of the skull to the origin of the esophagus. Portions of the pharynx lie posterior to the nasal cavity (nasal pharynx), oral cavity (oral pharynx), and larynx (laryngeal pharynx). The oral pharynx and laryngeal pharynx are shared for breathing and eating.

The muscular walls of the pharynx are formed of an outer layer made up of three circularly disposed muscles, the constrictors, and the inner muscular layer of the pharynx is made up of three small, longitudinally oriented muscles. During swallowing, successive contraction of the superior, middle, and inferior constrictor muscles helps to propel a bolus ball of food down into the esophagus. In addition, contraction of the three longitudinal muscles of the pharynx helps to raise the pharynx, effectively aiding it in engulfing the bolus of food.

The pharynx contains a "ring" of specialized lymphatic tissue designed to prevent the entry of pathogens into the digestive and respiratory tracts. This specialized lymphatic tissue is known as "tonsils" and is organized into three groups: nasopharyngeal tonsils (adenoids), located in the nasal pharynx; palatine tonsils (tonsils), located between the palatoglossal and palatopharyngeal folds in the oral pharynx; and lingual tonsils, located on the posterior surface of the tongue.

Fresh air in the alveoli presents high gaseous oxygen concentration and low gaseous carbon dioxide concentration to blood in the proximal pulmonary capillaries. Carbon dioxide moves from the blood in the proximal pulmonary capillaries to air in the alveoli (carbon dioxide is "blown off") and oxygen moves from air in the alveoli to hemoglobin molecules in the blood of the proximal pulmonary capillaries.

"Blue blood" in the proximal pulmonary capillaries becomes saturated, or "red blood", in the distal segments of these capillaries. Relaxation of the intercostals muscles, contraction of the muscles of the hemi-diaphragms, contraction of the muscles of the tongue, and relaxation of the muscles of the pharynx is a complex neuromuscular orchestration that occurs with each normal breath.

In addition, breathing centers in the medulla and pons integrate neural signals. The reticular formation, the nucleus retroambigualis, nucleus ambiguus, nucleus parambigualis, and the pre-Botzinger complex control voluntary forced exhalation and augment the force of inspiration. The nucleus tractus solitarius controls the timing of inspiratory movements. The pneumotaxic center fine tunes breathing rate, and the apneustic center in the lower pons controls breathing intensity. Further breathing integration occurs in the anterior horn cells of the spinal cord.

II. Sleep Apnea

"Apnea" is the technical term for suspension of breathing. During apnea there is no movement of the muscles of breathing and the volume of the lungs initially remains unchanged. Depending on the openness of the airways there may or may not be a flow of gas between the lungs and the environment. Apnea can be voluntarily achieved through breath-holding, drug-induced, mechanically induced (as in strangulation or obstructive sleep apnea), and caused by brain or spinal cord disease or injury (as in central sleep apnea).

II.A. Definition of Sleep Apnea

Sleep apnea is a sleep disorder characterized by pauses in breathing during sleep. Each apneic event lasts long enough so that one or more breaths are missed. Missed breaths occur repeatedly throughout sleep. Sleep apnea is definitively diagnosed with an overnight sleep test called a "polysomnogram." An apneic event includes an absence of air flow for 10 second or longer, with either a neurological arousal (a 3-second or greater shift in EEG frequency) or a blood oxygen desaturation of 4% or greater, or both.

In addition to complete cessation of breathing, individuals with sleep apnea also exhibit smaller than normal breaths or "hypopneas." Hypopneas in adults are defined as a 50% reduction in air flow that occurs for more than 10 seconds, followed by a 4% desaturation in blood oxygen or neurological arousal, or both. Since both apneas and hypopneas are detrimental to sleep, the Apnea-Hypopnea Index (AHI) was created to measure the overall severity of sleep apnea by counting the number of apneas and hypopneas that occur per hour of sleep. The categorization of normal and abnormal states is shown in Table I.

TABLE I

Apenea-Hypopnea Index (AHI)

| AHI | Rating |
|---|---|
| <5 | Normal |
| 5 to 15 | Mild |
| 15 to 30 | Moderate |
| >30 | Severe |

II.B. Signs and Symptoms of Sleep Apnea

1. Frequent cessation of breathing (apnea) during sleep often noticed by one's sleep partner.
2. Choking or gasping during sleep to get air into the lungs
3. Loud snoring
4. Sudden awakenings to restart breathing
5. Waking up in a sweat during the night
6. Feeling fatigued in the morning after a night's sleep
7. Headaches, sore throat, or dry mouth in the mornings after waking up
8. Exaggerated daytime sleepiness, including falling asleep at inappropriate times, such as during driving or at work Individuals with sleep apnea are rarely aware of having difficulty breathing, even upon awakening. Sleep apnea is recognized as a problem by others witnessing the individual during episodes or is suspected because associated abnormalities seen elsewhere in the body. Symptoms may be present for years, even decades without identification, during which time the sufferer may become conditioned to the daytime sleepiness and fatigue associated with significant levels of sleep deprivation.

II.C. Risk factors of Sleep Apnea

1. Nasal, oral, pharyngeal, or laryngeal anatomic or physiologic abnormalities including large tonsils or adenoids, chronic nasal congestion, deviated nasal septum, enlarged tongue, receding chin, enlarged soft palate, or lengthened uvula.
2. Excess fat deposit surrounding the pharynx
3. Family history of sleep apnea
4. Old age
5. Male gender (1, 2)

II.D. Sequela of Sleep Apnea

Mild, occasional sleep apnea, such as many people experience during an upper respiratory infection, may not be important. However, chronic, severe obstructive sleep apnea requires treatment to prevent sleep deprivation and other medical complications, including death.

II.D.1. Sleep Deprivation

Both the person with sleep apnea and the bed partner suffer from sleep deprivation. A bed partner may lose an hour or more of sleep each night from sleeping next to a person with sleep apnea. Along with the apnea episodes, the person afflicted with sleep apnea may have additional trouble sleeping caused by side effects of the condition, including a frequent need to get up and urinate during the night, and excessive nighttime sweating.

II.D.2. Oxygen Deprivation

When you stop breathing, your brain does not get enough oxygen. Drastic problems can result from the oxygen deprivation of sleep apnea, including premature death.

In some individuals, elevated systemic arterial pressure (commonly called high blood pressure) is a sequela of obstructive sleep apnea syndrome(3) When high blood pressure is caused by OSA, it is distinctive in that, unlike most cases of high blood pressure (so-called essential hypertension), the pressure readings do not drop significantly when the individual is sleeping.(4) OSA is associated with signs of cardiac ischemia and cardiac rhythm disturbances. (5). Stroke and even premature death are associated with obstructive sleep apnea.(6)

Individuals suffering from OSA show brain tissue loss in regions that help store memory, thus linking OSA with memory loss.(7)

II.D.3. Metabolic Imbalances

Obstructive sleep apnea is associated with a range of metabolic abnormalities. (8-18). For example, the hormone adiponectin is decreased in concentration in the serum in patients with sleep apnea. This hormone affects: glucose flu; gluconeogenesis; glucose uptake; lipid catabolism; b-oxidation; triglyceride clearance; insulin sensitivity; and protects endothelium from artherosclerosis.

II.D.4. Depression

Approximately one in five people who suffer from depression also suffer from sleep apnea, and people with sleep apnea are five times more likely to become depressed. Existing depression may also be worsened by sleep apnea. Treating sleep apnea may alleviate depression in some people.

II.E. Types of Sleep Apnea

There are three distinct forms of sleep apnea: obstructive; central; and mixed, which is a combination of the two. These three types comprise 84%, 0.4%, and 15% of cases, respectively.(19) Clinically significant levels of sleep apnea are defined as five or more episodes per hour of any type of apnea as identified on a polysomnogram. In obstructive sleep apnea, breathing is interrupted by a physical block to airflow despite contraction of the hemi-diaphragms. Breathing is interrupted by the absence of effort in central sleep apnea. In mixed sleep apnea, there is a transition from central to obstructive features during the apneic events themselves.

III. Obstructive Sleep Apnea (OSA)

The clinical picture of obstructive sleep apnea was first characterized as a personality trait and called the "Pickwickian syndrome." This term was coined by the famous early 20th Century physician, William Osler, to match the description of Joe, "the fat boy" in Dickens's novel, The Pickwick Papers. Dickens's description is an accurate clinical picture of the adult obstructive sleep apnea syndrome.

The early reports of obstructive sleep apnea in the medical literature described individuals who were very severely affected, often presenting with severe hypoxemia (low $O_2$), hypercapnia (increased $CO_2$) and congestive heart failure. Tracheostomy was the recommended treatment. Though it could be life-saving, post-operative complications in the tracheostomy stoma were frequent in these very obese and short-necked individuals. That a tracheotomy can effectively treat even severe obstructive sleep apnea implies that the anatomic site or sites of obstruction of the airway during sleep are above or superior to the level of the trachea. Historically, however, tracheostomies have involved the implantation of devices inside the trachea, which impedes air movement and can induce other complications.

III.A. Sites of Obstruction

Obstruction of the airway at the level of the nasal cavity, the anterior tongue, the bony jaw, the tonsils, and the adenoids are relatively straightforward to diagnose and can often be accurately identified clinically. The real difficulty in obstructive sleep apnea is identifying the level of obstruction in the pharynx during sleep. Normally, muscles in the body relax during sleep, including those of the pharynx. When relaxed the pharynx is composed of collapsible walls of soft tissue which can obstruct breathing. During each breath, the muscles of the pharynx contract in a coordinated fashion to "open" the pharynx and allow air to flow through.

The pharynx can be identified by lateral radiography, computed tomography (CT), magnetic resonance imaging (MRI), and fluoroscopy.(20) Of these modalities, CT and MRI provide cross sectional images and are the most accurate measurements of pharyngeal narrowing.

III.A.1. Oropharynx

Many studies of patients with obstructive sleep apnea have placed the primary locus of obstruction in the oropharynx. (21-25)

III.A.2. Nasopharynx

Other studies place the primary site of pharyngeal narrowing superior to the oropharynx. (26, 27)

III.A.3. Diffuse

Still others have found that pharyngeal obstruction can be at one location in one individual and at another location is a different person.(28-31)

III.B. Treatment

III.B.1. Minor Treatments

III.B.1.a). Lifestyle Changes

Alcohol avoidance, cessation of the use of muscle relaxants and sleep medications, weight loss, and quitting smoking may each diminish the severity of obstructive sleep apnea. Life style changes are most effective in patients with mild obstructive sleep apnea.

III.B.1.b). Dental Appliances

Some people benefit from various kinds of oral appliances to keep the upper airway open during sleep. An oral appliance is a custom made mouthpiece that shifts the jaw forward to help keep the pharynx open during sleep. Oral appliance therapy is usually successful in patients with mild to moderate obstructive sleep apnea.

III.B.1.c). Sleep Posture

Many people benefit from a change of sleep posture.(32-37) For example, sleeping at a 30 degree elevation of the upper body or higher, or sleeping on one's side, may help to prevent the gravitational collapse of the phayrngeal airway.

III.B.1.d). Medication

Medications like Acetazolamide lower blood pH and encourage breathing. Low doses of oxygen are also used as a treatment for hypoxia.

III.B.1.e). Wind Instruments

A recent study found that learning and practicing the didgeridoo wind instrument helped reduce snoring and sleep apnea, as well as daytime sleepiness. This appears to work by strengthening muscles in the upper airway, thus reducing their tendency to collapse during sleep.(38)

III.B.2. Major Treatments

III.B.2.a) Continuous Positive Airway Pressure (CPAP)

III.B.2.a).(1) CPAP Benefits

The management of obstructive sleep apnea was revolutionized with the introduction of continuous positive airway pressure by Sullivan.(39-42) The first models were bulky and noisy but the design was rapidly improved and, by the late 1980s, CPAP was widely adopted. The availability of an effective treatment stimulated an aggressive search for affected individuals and led to the establishment of hundreds of specialized clinics dedicated to the diagnosis and treatment of sleep disorders. The vast majority of patients who attend a sleep clinic suffer from a sleep apnea.

III.B.2.a).(2). CPAP Failures

Though CPAP therapy has brought relief from obstructive sleep apnea to many, it is not without complications. Table II lists the common complaints made by patients on CPAP therapy.

TABLE II

Common problems reported with nasal continuous positive airway pressure and trouble-shooting guide

| Problem Complex | Possible Cause | Correction |
| --- | --- | --- |
| Mask Leaks Skin Irritation Pressure sores or blisters | 1. Strap adjustment too loose or too tight 2. Incorrect mask size | 1. Readjust headgear straps. The mask should be as loose as possible while still creating a seal |

TABLE II-continued

Common problems reported with nasal continuous positive airway pressure and trouble-shooting guide

| Problem Complex | Possible Cause | Correction |
|---|---|---|
| | 3. Worn-out mask<br>4. Dirty mask | 2. Consult respiratory therapist for a mask fitting. Nasal pillows or full-face mask may provide a better fit<br>3. Inspect mask for stiffness, cracks or breaks. Replace mask if needed<br>4. Wash mask daily; wash face nightly |
| Dry nose and/or throat. Nasal Congestion Epistaxis | 1. Dry air | 1. Try nasal saline spray before bedtime and upon awakening<br>2. Add heated humidification<br>3. Try topical nasal steroid preparation or antihistamines<br>4. May have some desensitization over time<br>5. Consult physician if symptoms persist |
| Dry mouth | 1. Sleeping with mouth open | 1. Try a chin strap<br>2. If this is not helpful, a full-face mask may be considered<br>3. Add heated humidification |
| Sore, dry, irritated or swollen eyes, conjunctivitis | 1. Mask leaks<br>2. Mask too tight | 1. Try reseating the mask on the face<br>2. Readjust headgear straps.<br>3. Inspect mask for stiffness, cracks or breaks. Replace mask if needed.<br>4. Use an eye patch |
| Rhinorrhea | 1. Dry air | 1. Try saline nasal spray before bedtime<br>2. Try topical nasal steroid preparation or intranasal ipratropium bromide before bedtime<br>3. Add heated humidification |
| Allergic rhinitis | 1. Irritants drawn in with room air through machine | 1. Place unit on bedside table to keep dust and/or animal hairs out of machine<br>2. Consult respiratory therapist: a fine particulate filter can be added to some units<br>3. Add heated humidification<br>4. Consult physician if symptoms persist (may require medication) |
| Chest discomfort Aerophagia Sinus discomfort Difficulty exhaling | 1. Pressure requirement may be lower at beginning of sleep period<br>2. Initial adjustment period | 1. Try pressure ramp at beginning of sleep period<br>2. Reduce pressure with bilevel positive airway pressure<br>3. Try to reduce pressure requirement by using oral appliance and CPAP (no data available) |
| CPAP unit too noisy | 1. Blocked air intake<br>2. Too close to sleeping area | 1. Check if air filter is clean and not blocked by outside items<br>2. Add a length of hose and place unit farther away |
| Bed partner intolerance | 1. Multiple factors (noise, anxiety) | 1. Promote education of the patient and bed partner<br>2. Recommend attending a patient support group (i.e., A.W.A.K.E. Network of the American Sleep Apnea Association) |

III.B.2.b). Surgery

Specific types of surgery can increase the size of the pharyngeal, oral, and nasal airways by removing or reshaping tissues. (43) A surgeon may remove tonsils, adenoids, or excess tissue at the back of the throat or inside the nose. A surgeon may even reconstruct the jaw to enlarge the pharynx.

IV. Central Apnea

Any individual, no matter how healthy, when given enough of a central respiratory depressant, will develop central apnea. In large amounts, alcohol is a central respiratory depressant, and so are opiates, barbiturates, benzodiazepines, and many other tranquilizers and sleep aids.

Central sleep apnea (CSA), the rarest type of sleep apnea, occurs when the brain signals that instruct the body to breathe are delayed. This central nervous system disorder can be caused by disease or injury involving the brainstem, such as a stroke, a brain tumor, a viral brain infection, or a chronic respiratory disease. People with CSA seldom snore, which makes it even harder to diagnose as they do not fit the "normal" profile of a sleep apnea sufferer. However, while the causes of the breathing cessation are different in central sleep apnea and obstructive sleep apnea, the symptoms and results are much the same. Patients are deprived of oxygen and repeatedly awaken at night. The treatments for CSA include specific medications that stimulate the need to breathe and administrations of oxygen.

Central sleep apnea usually occurs most commonly in people who are seriously ill. For example, it can occur in people with a variety of severe and life-threatening lower brain stem lesions. Since the brainstem controls breathing, any disease or injury affecting it may result in apnea, even when awake.

Conditions that can cause central sleep apnea include:
1. Bulbar poliomyelitis
2. Encephalitis affecting the brainstem
3. Neurodegenerative illnesses 4. Stroke affecting the brainstem 5. Cervical spine injury

IV.A. Definition

In pure central sleep apnea, the brain's respiratory control centers do not function normally during sleep. The concentration of carbon dioxide in the blood and the neurological feedback mechanism that monitors it do not react quickly enough to maintain an even respiratory rate, with the entire system cycling between apnea and rapid breathing (hyperpnea), even during wakefulness. The sleeper stops breathing, and then starts again. There is no effort made to breathe during the pause in breathing; there are no chest movements and no struggling. After an episode of apnea, breathing may be faster for a period of time, a compensatory mechanism to blow off carbon dioxide and absorb more oxygen.

The immediate effects of central sleep apnea on the body depend on how long the failure to breathe endures. At worst, central sleep apnea may cause sudden death. Short of death, drops in blood oxygen may trigger seizures—even in the absence of epilepsy. In people with epilepsy, the hypoxia caused by apnea may trigger seizures that had previously been well controlled by medications. In other words, a seizure disorder may become unstable in the presence of sleep apnea. In adults with coronary artery disease, a severe drop in blood oxygen level can cause angina, arrhythmias, or myocardial infarction. Longstanding recurrent episodes of apnea, over months and years, may cause an increase in carbon dioxide levels that can change the pH of the blood enough to cause a metabolic acidosis.

IV.B. Treatment

IV.B.1. Stop CNS Depressant Drugs

IV.B.2. Pace the Diaphragms

When central apnea is severe, the diaphragm can be artificially paced with electrical currents (Synapse Biomedical, Inc, Oberlin, Ohio). Surgically implanted electrodes electrically stimulate the phrenic nerve or the muscles of the hemidiaphragms, directly. Wires from the electrodes in the diaphragm run to and from a control box worn outside the body. The pacing is performed according to a reconditioning program in which the duration and frequency of electrode stimulation is gradually increased until full-time diaphragm pacing is achieved. When the electrodes are stimulated by current, the diaphragm contracts and air is sucked into the lungs (inspiration). When the electrodes are not stimulated, the diaphragm relaxes and air moves out of the lungs (expiration).

V. Mixed Apnea and Complex Sleep Apnea

Some people with sleep apnea have a combination of obstructive and central sleep apnea. (19) When obstructive sleep apnea is severe and longstanding, episodes of central apnea sometimes develop. The exact mechanism of the loss of central respiratory drive during sleep in obstructive sleep apnea is unknown.

Complex sleep apnea has recently been described by researchers as a novel presentation of sleep apnea. Patients with complex sleep apnea exhibit OSA, but upon application of positive airway pressure, the patient exhibits persistent central sleep apnea. This central apnea is most commonly noted while on CPAP therapy, after the obstructive component has been eliminated.

VI. Conclusion

What is needed in sleep apnea is an integrated medical device system that can treat all forms of sleep apnea with minimal interference with a person's night-time sleeping experience.

Two primary problems exist for patients with sleep apnea: absence of breathing effort and obstruction of air flow. Absence of breathing effort can be treated with electrical pacing of the diaphragm. Obstruction of air flow can be treated with bypass of the pharynx, oral cavity, and nasal cavity airways, as in the creation of a tracheostomy, or by briefly opening obstructive zones within the upper airway with electrical stimulation of the muscles at the site or sites of obstruction. To be effective, the pacing of the diaphragms and the pacing of upper airway muscle contractions would have to be coordinated. The pacing of the diaphragms and bypass of the upper airway would not have to be coordinated.

SUMMARY

According to a first aspect of the invention, a nasal-pharyngeal bypass useful for establishing an airway for the patient, the bypass comprises a collapsible tube having a proximal end, a distal end, a lumen extending through the tube, and a length between the proximal and distal ends so that, when the tube is inserted through the patient's nostril, through the patient's nasal cavity, and into the patient's throat, the distal end of the tube is above the patient's epiglottis and the proximal end of the tube is outside of the patient's nostril, wherein the tube has a collapsed configuration in which the tube is sized to be inserted through the patient's nasal cavity, and wherein the tube has an expanded configuration in which the tube is sized to be retained in the patient's nasal cavity and establish a bypass airway for the patient through the lumen of the tube.

According to another aspect of the present invention, a method of treating sleep apnea in a patient comprises selecting a collapsible tube having a length so that, when the tube is inserted through the patient's nostril, through the nasal cavity, and into the patient's throat, a distal end of the tube is above the patient's epiglottis and a proximal end of the tube is outside of the patient's nostril, inserting the collapsible tube, in a collapsed configuration, through the patient's nostril, through the patient's nasal cavity, and into the patient's throat, with the distal end of the tube above the patient's epiglottis and the proximal end of the tube outside of the patient's nostril, and causing the tube to expand into an at least partially un-collapsed configuration.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which:

FIG. 9 illustrates a perspective exploded view of a fifth exemplary embodiment;

FIG. 10 illustrates a perspective view of the embodiment of FIG. 9, in an unrolled configuration;

FIG. 11 illustrates a side elevational view of the embodiment of FIG. 9, in an unrolled configuration;

FIG. 12 illustrates an enlarged side elevational view of portion A of FIG. 11;

FIG. 13 illustrates a perspective view of the embodiment of FIG. 9, in a rolled and uninflated configuration;

FIG. 14 illustrates a perspective view, similar to that of FIG. 13, of the embodiment of FIG. 9 in a rolled and inflated configuration; and FIG. 15 illustrates an end elevational view of the embodiment of FIG. 9, in a rolled and inflated configuration.

DETAILED DESCRIPTION OF EXEMPLARY EMBODIMENTS

Figure 1:
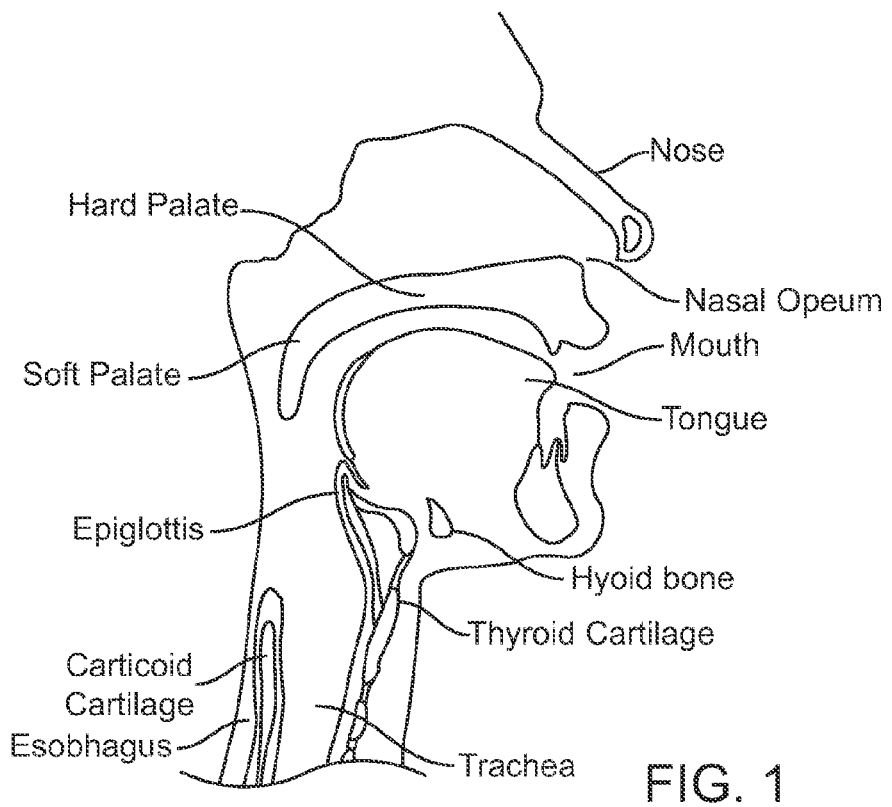
FIG. 1 illustrates anatomical structures of the mouth, nasal cavities, throat, and adjacent structures.

Referring to the drawing figures, like reference numerals designate identical or corresponding elements throughout the several figures.

The majority of cases presenting to physicians for treatment are Obstructive Sleep Apnea (OSA) in which the cause of the obstruction is airway closure due to tissue relaxation within the nasal cavity, anterior tongue, tonsils, adenoids, nasopharanx (soft palate), oropharanx (base of the tongue), or diffuse (multiple areas) (see FIG. 1).

Placement of a nasal-pharyngeal bypass tube embodying principles of the present invention is similar to the routine placement of a standard nasogastric tube or nasotracheal tube. At least two differences exist between the nasal-pharyngeal bypass tubes of the present invention and those two standard tubes: (1) a nasal-pharyngeal bypass tube of the present invention is much shorter than a standard nasogastric tube or nasotracheal tube, being just long enough to clear the soft tissue posterior to the tongue but short enough to terminate before reaching the level of the epiglottis; and (2) a nasal-pharyngeal tube of the present invention has a flange or other retaining device at its proximal end to stop the nasal-pharyngeal from advancing further into or from falling out of the nasal cavity.

Each nasal-pharyngeal bypass tube of the present invention would be "fitted" by imaging or other methods to create a tube length specific to each patient. A small flexible lyringoscope or bronchoscope could optionally be passed through the nasal cavity and a scale along its length utilized to size the required airway to the proper position above the epiglottis. Further, internal tube luminal diameter is matched to the respiratory flow needs of each patient and the nasal passage size.

To position a nasal-pharyngeal tube in accordance with the present invention, the distal end of the tube is preferably lubricated with an analgesic jelly at the nasal opening. The tube could also have additional analgesic jelly applied and inserted into one of the patient's anterior nostrils. The tube is then pushed through the nasal cavity and down into the throat. Once the distal end of the tube has passed the pharynx, the tube is in the correct position. The proximal flange or similar retention device would prevent further descent of the nasal-pharyngeal tube. An adhesive flange can alternatively be used to retain the nasal-pharyngeal tube in place during sleep so that it does not back out of its desired position.

It expected that a patient will place the nasal-pharyngeal tube in a nostril prior to sleep and remove the tube upon waking in the morning. Alternating nostril use would mitigate nasal irritation. For some, an oral-pharyngeal bypass tube might be preferable with an oral retaining device.

The construction of a naso-pharyngeal tube embodying principles of the present invention also differs from those currently available. Currently available tubes are used during oral surgery to maintain an airway for the patient without increasing the complexity of a normal endo-tracheal tube being in place. Some existing products are intended for emergency use to maintain an open airway. Others are clearly designed and intended for intubation during surgery. The common factor in the design is that the tube is constructed of a flexible material and meant to be inserted by a caregiver while the patient may be somewhat anaesthetized. Also, these tubes are not intended for chronic care where they would be utilized nightly and as such they may induce some irritation in nightly use.

Different from those naso-pharyngeal tubes currently available, tubes embodying principles of the present invention are instead designed and intended for nightly use and to be patient-applied, while it is desirable for the device to be disposable and intended for single use. The repeated use of a tube running through and across delicate mucous membranes will have some irritating effects, and therefore it can be particularly advantageous, yet still optional, for the device to create a very soft and pliable airway which is easy to install and minimally irritating.

The materials of choice include soft thermoplastic rubbers, such as C-Flex, or thermoset materials such as silicone, or hydrogels which become very soft as they hydrate. The construction can include a coated spring body or other composite techniques to prevent collapse of the airway as tissue impinges upon it. Alternately, a construction could be chosen that makes for easy insertion by the patient, but includes a non-irritating coating to minimize long term problems associated with nightly use. A desired outcome of the use of the device is to support the tissue and maintain an open airway through the typical anatomy that collapses nightly leading to OSA. Airflow is primarily within the lumen of the device, although some additional flow around the device may occur is the tissue is not allowed to collapse.

In general terms, systems and methods embodying principles of the present invention attempt to overcome existing limitations to therapy by providing a system that can maintain the patency of the airway as tissue relaxes and collapses. While devices in accordance with the present invention can share some attributes with existing naso-pharyngeal tubes, they are structurally and functionally different. Exemplary devices extend from the nasal opening, through the nasal cavity, support the soft palate, and extend down the orophananx to support the tongue; see FIGS. 1 and 2. The distal end of the device would be placed just superior to the epiglottis. The product is advantageously soft enough to be self-placed by a patient, has adequate "hoop" strength to prevent collapsing as tissue relaxes and collapses onto the device, and bridges all of the major structures to support the airway. Optionally, the device is constructed so that it can be collapsed or is small for easy installation, and then expands or enlarges to produce a larger inner pathway through the device after installation. Thus, in general terms, certain embodiments relate to a patient-applied naso-pharyngeal tube constructed and fitted with components to allow a sleep apnea sufferer to self-apply the device nightly, and the device is preferably removed by the patent in the morning. The device can be disposable daily, weekly, or monthly depending on the materials or use and construction. Daily cleaning may be useful with a periodic disinfection. The device is advantageously sized to support the airway from the nasal opening through the soft palate, pharanx, and at the base of the tongue, but not to enter the trachea.

By way of example and not of limitation, one exemplary embodiment includes a single tube of approximately 3/16 inch to 1/4 inch internal diameter (ID) and constructed to prevent the collapse described herein, should provide adequate airflow. The length of the device would be tailored to each individual's anatomy by a physician so that it can maintain the patency of the airway during sleep. Exemplary materials for a device range from vinyl in the tubing to thermoplastic elastomers (e.g., e-flex) or thermoset materials such as silicone. A blend of material properties is needed to provide flexibility for installation, columnar strength for pushability for installation, and hoop strength to prevent collapse and support the surrounding tissue. The length of the tube would vary due to individual patient anatomy. The length would likely range from about 5 to 9 inches for adults, while the distal end of the device would not enter the trachea and advantageously remains above the epiglottis.

The tube is alternatingly installed in either naris (nostril) nightly to minimize or prevent erosion or excessive inflammation due to its placement and use. Additional materials could include hydrogels which would be stiff for introduction and installation of the device, but softer in situ with the humid air from respiration. These materials can be optionally internally supported with a spring-like structure.

Figure 2:
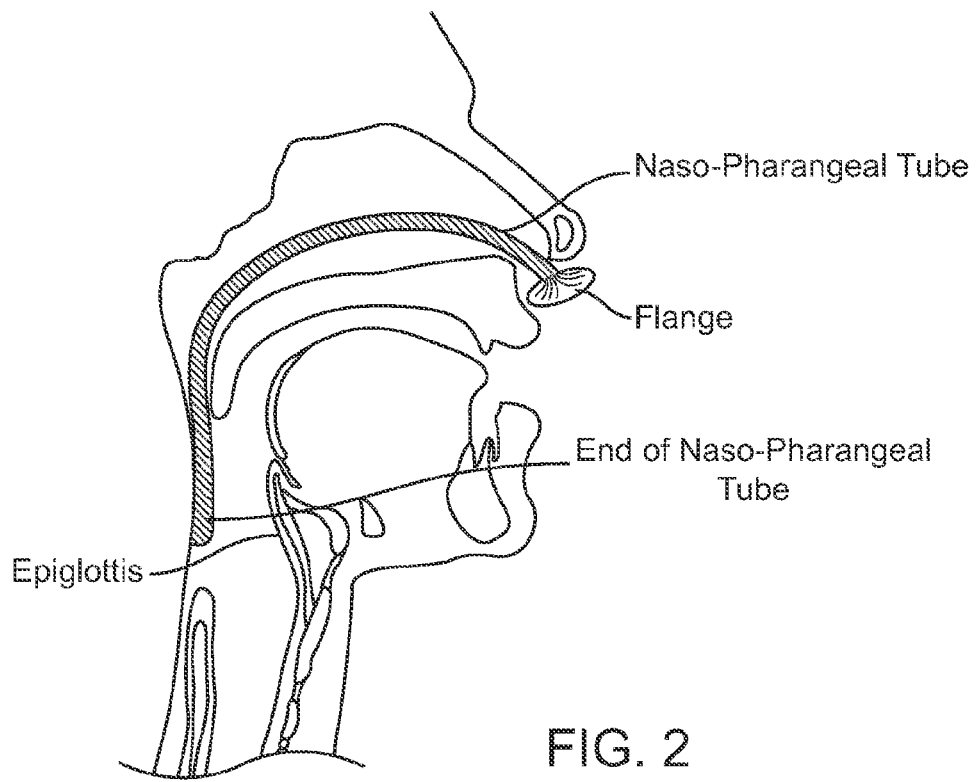
FIG. 2 illustrates an exemplary device positioned through the nasal passages of a patient.

The tube advantageously, yet optionally, includes a retention device at its proximal end, which may include a flange, an adhesive flange, or a clip for attaching the tube to the nostril to prevent the device from sliding internally; see FIG. 2.

Figure 3A:
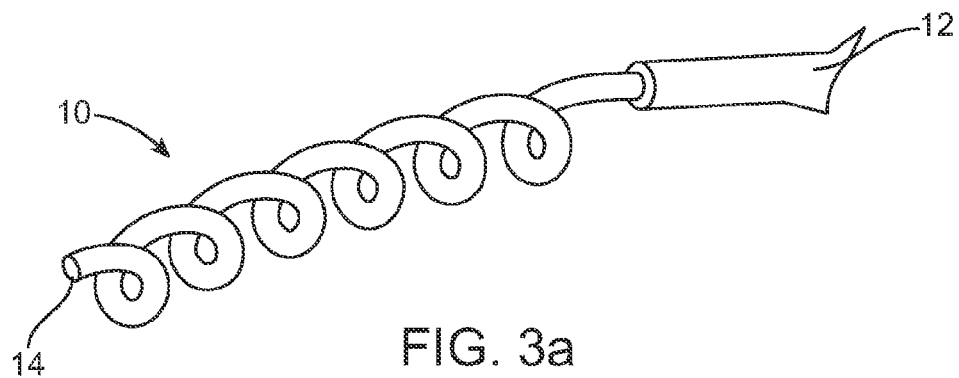
FIGS. 3a and 3b illustrate a second exemplary embodiment, including a helical tube.
Figure 3B:
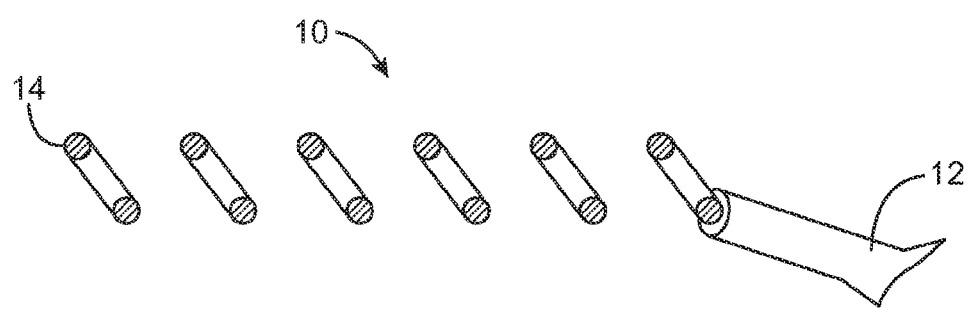
Figure 4:
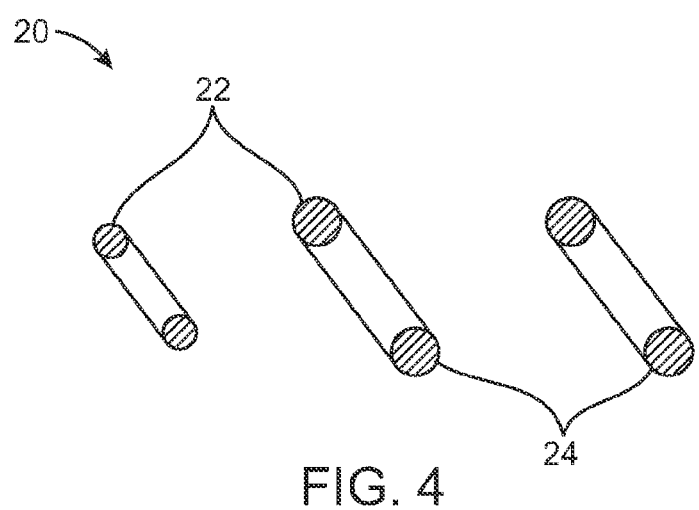
FIG. 4 illustrates a longitudinal cross-sectional view of a third exemplary embodiment, also including a helical tube.
Figure 5:
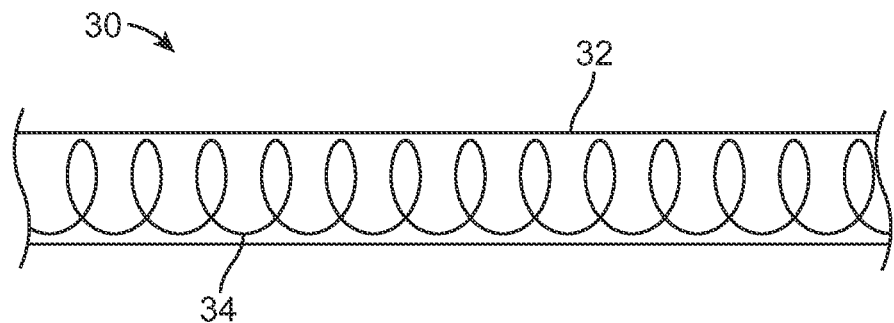
FIG. 5 illustrates a side elevational view of a fourth exemplary embodiment.
Figure 6:
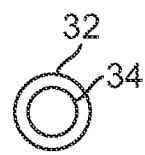
FIG. 6 illustrates a left side end view of the embodiment of FIG. 5.

Other exemplary embodiments 10, 20, illustrated in FIGS. 3a, 3b, and 4, include a helically-wound inflatable structure, e.g., a balloon, that is in a collapsed (un-inflated or only partially inflated) configuration during installation and then expanded (inflated more, including completely inflated) after placement. The inflating wall of the helical tube would cause the collapsed device to expand and lengthen, creating a helical support structure. The tube 10 optionally includes a check valve 12 at one end, to hold fluid pressure in the tube, and a sealed end 14 opposite the check valve 12. Preferably, the check valve 12 is on the proximal end of the tube 10. FIG. 3b, which is a longitudinal cross-sectional view of the tube 10, shows the sealed end 14 opposite the check valve 12 when in an inflated configuration.

Another exemplary embodiment, see FIG. 4, includes a helically constructed flat balloon 20, including an inner surface 24 constructed of a relatively thin, non-compliant material such as polyester, and an outer wall 22 formed of or including a thin layer of a soft, elastic material, such as polyurethane. The edges can be heat sealed or bonded and, when the balloon 20 is inflated, the structure behaves similar to a bimetallic spring, with the outer layer stretching and the inner layer resisting the stretch, causing the tube 20 to take on a non-linear orientation when inflated.

Figure 7A:
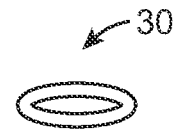
FIGS. 7a and 7b illustrate left side end views, similar to that of FIG. 6, of the embodiment of FIG. 5 in collapsed (FIG. 7a) and folded (FIG. 7b) configurations.
Figure 7B:
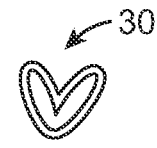
Figure 8:
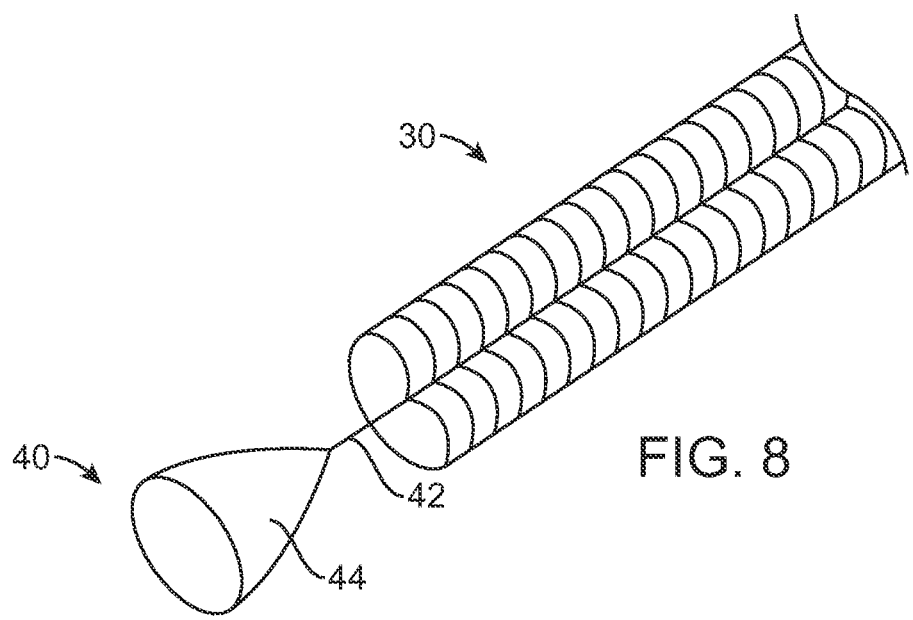
FIG. 8 illustrates the embodiment of FIG. 5 with an exemplary mandrel.

Other constructions are possible according to principles of the present invention. By way of non-limiting example, and with reference to FIGS. 5-8, an exemplary device 30 includes a tube 32 constructed over a helical spring 34. The spring is advantageously, yet optionally, coated with a soft polymer, such as silicone or polyurethane, to create a tube. This tube is then collapsed (FIG. 7a) and folded (FIG. 7b) to form an axially folded, roughly V-shaped compound structure. A mandrel 40 is then inserted from the distal end of the device 30 and includes a long, relatively rigid wire or stylet which 42 which runs the entire length of the folded structure, exiting at the proximal end flare, which is not collapsed. After installation of the folded tube into the patient, the mandrel 40 is withdrawn through the collapsed tubing, a distal end piece 44, which is attached to the stylet 42 and which is preferably conically shaped, expanding the tube 30 in place to create and support the airway. The mandrel 40 can then be discarded. The construction of the tube 30 is such that, once expanded by the mandrel 40, the tube stays in the expanded configuration.

Thus, devices embodying principles of the present invention are intended to perform two functions simultaneously: keeping an open airway through an inner lumen of the device; and support for the tissue in the airway, because keeping the tissue from completely collapsing creates the possibility of some air movement around the device in the critical areas associated with obstructive sleep apnea.

FIGS. 9-12 illustrate yet another exemplary device 50 embodying principles of the present invention, in an exploded view. The device 50 includes two sheets 52, 54 of a biocompatible material, which are the same shape. Each sheet includes a proximal end 62, a distal end 64, and a center portion 66. While the sheets 52, 54 can take any shape, they are advantageously generally rectangular, with the distal end 64 and the proximal end 62 optionally narrower than, and further optionally tapered from, the center portion 66.

A stiffening mandrel 56 extends and is sandwiched or otherwise held between the two sheets 52, 54, and includes an elongate shaft 80 and a distal, olive-shaped obturator tip 82. The mandrel 56 can be formed of any suitable material which is stiff enough to provide rigidity to the device 50 sufficient for the device to be positioned as described herein, and is optionally formed of a malleable material.

A valve 58, which is advantageously a reed valve, is positioned adjacent to the proximal end 62. When a reed valve is used for valve 58, the valve includes a pair 76, 78 of valve elements which permit an inflation tube 60 to be inserted into the proximal end of the valve, so that an inflation fluid, e.g., air, saline, or the like, can be injected into a space between the sheets 52, 54, as described in greater detail below.

In an assembled state, as illustrated in FIG. 10, the sheets 52, 54 are positioned against each other, and the sheets are jointed together. In a particularly advantageous embodiment, a weld seam 68 joins the sheets 52, 54 together, and also forms an inflation cavity, balloon, or bladder 70 between the sheets. As illustrated in FIG. 12, the inflation seam 68 optionally also can be used to secure the valve 58 in place between the sheets 52, 54. Also illustrated in FIGS. 10 and 11, the weld seam 68 can be shaped to optionally, yet advantageously, form a plurality of elongated inflated fingers 72 which are all fluidly connected together, which aid the structure and integrity of the device 50 during use. In the embodiment illustrated in FIGS. 10 and 11, the fingers 72 are oriented generally perpendicular to the length of the stiffening mandrel 54; however, the fingers 72 can be oriented in other directions. The weld seam 68 is preferably a loop, that is, the seam has two ends which are close to each other; however, a plurality of weld seams that join together can also be used to form the inflation cavity 70.

As illustrated in FIGS. 11 and 12, the mandrel 56 is held in the device 50, such as by joining together the bottom edges 74 of the sheets 52, 54, thus capturing the mandrel between a portion of the weld seam 68 and the bottom edges 74. In the embodiment illustrated in FIGS. 11 and 12, the mandrel 56 is fixed in the device 50. According to another exemplary embodiment, the space between the joined bottom edges 74 of the sheets 52, 54 and the weld seam 68 forms a lumen 84 (FIG. 12) through which the mandrel 56 is free to slide. Also illustrated in FIG. 12, the inflation tube 60 advantageously includes a blunt tip 86 to assist in inserting the tube into the valve 58.

Turning now to FIGS. 13-15, further features and uses of the device 50 will be described in which FIG. 13 illustrates a perspective view of the embodiment of FIG. 9, in a rolled and un-inflated configuration; FIG. 14 illustrates a perspective view, similar to that of FIG. 13, of the embodiment of FIG. 9 in a rolled and inflated configuration; and FIG. 15 illustrates an end elevational view of the embodiment of FIG. 9, in a rolled and inflated configuration. As illustrated in FIGS. 13 and 14, the mandrel 56 optionally includes a bent portion 92 between its two ends, to assist in maneuvering and positioning the device 50 as illustrated in FIG. 2. When the mandrel 56 is formed at least partially of a malleable material, the shape of the mandrel can be changed to suit the particular patient.

FIG. 13 illustrates the device 50 with the sheets 52, 54 forming a flat balloon rolled up around the mandrel 56, thus positioning an outer surface 96 (FIG. 15) of one of the sheets as an outer surface of a tube and the outer surface 94 of the other of the sheets as an inner surface of a tube. In this configuration, and when the fingers 72 extend perpendicular to the mandrel 56, the fingers 72 extend circumferentially around the device 50. The device is advantageously heat set in an oven, or is otherwise made to maintain its minimal, tubular profile, which can ease introduction of the device 50 into the nasal passage. The rolled balloon-tube device is optionally lubricated and placed into the nasal passage up to or through the oral pharynx, as described elsewhere herein and illustrated in FIG. 2. Once in place, a syringe or other fluid delivery device attached to the proximal end of the inflation tube 60 and is used to inflate the balloon by injecting fluid into the cavity 70. The introduction of fluid in the cavity 70 causes the device 50 to at least partially unfurl, creating a tube-like passage 98 for air to flow through and keep soft tissue from collapsing and blocking the patient's airway. The upper edge 90 of the sheets 52, 54, is not joined to the rest of the device 50, thus permitting the device to furl and unfurl. The fill tube is optionally removed and then the valve seals the fluid within the cavity 70.

The sheets 52, 54 can be formed of one or more of numerous materials. Polyester works well for the structure, but some types of polyester can be too stiff to install in the nasal passage. Similarly, some versions of polyethylene can be too stiff, but very thin linear low density polyethylene of 0.0005 to 0.001 inch thickness can be used. Ethylene vinyl alcohol (EVA) and polyurethane are also suitable materials and can be useable at wall thicknesses approaching 0.006 inch.

In accordance with yet another embodiment, the inflatable portion of any of the devices described herein can at least partially, optionally entirely, be formed of a permeable material. The inflation fluid can include a therapeutic agent, e.g., an antibiotic, analgesic, medicament, or any other such substance, to which the inflatable portion is permeable, so that, when any of the devices described herein is positioned as illustrated in FIG. 2, the therapeutic agent permeates through the inflated portion and is delivered to the tissues, e.g., mucosal membranes, of the patient.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the documents cited herein is incorporated by reference.

Reference List

1. Hader C, Schroeder A, Hinz M, Micklefield G H, Rasche K. Sleep disordered breathing in the elderly: comparison of women and men. J Physiol Pharmacol 56 Suppl 4:85-91, 2005.

2. Shepertycky M R, Banno K, Kryger M H. Differences between men and women in the clinical presentation of patients diagnosed with obstructive sleep apnea syndrome. Sleep 28:309-14, 2005.

3. Silverberg D S, Iaina A, Oksenberg A. Treating obstructive sleep apnea improves essential hypertension and quality of life. Am Fam Physician 65:229-36, 2002.

4. Grigg-Damberger M. Why a polysomnogram should become part of the diagnostic evaluation of stroke and transient ischemic attack. J Clin Neurophysiol 23:21-38, 2006.

5. Alonso-Fernandez A, Garcia-Rio F, Racionero M A, Pino J M, Ortuno F, Martinez I, Villamor J. Cardiac rhythm disturbances and ST-segment depression episodes in patients with obstructive sleep apnea-hypopnea syndrome and its mechanisms. Chest 127:15-22, 2005.

6. Yaggi H K, Concato J, Kernan W N, Lichtman J H, Brass L M, Mohsenin V. Obstructive sleep apnea as a risk factor for stroke and death. N Engl J Med 353:2034-41, 2005.

7. Kumar R, Birrer B V, Macey P M, Woo M A, Gupta R K, Yan-Go F L, Harper R M. Reduced mammillary body volume in patients with obstructive sleep apnea. Neurosci Lett 438: 330-4, 2008.

8. Magalang U J, Cruff J P, Rajappan R, Hunter M G, Patel T, Marsh C B, Raman S V, Parinandi N L. Intermittent Hypoxia Suppresses Adiponectin Secretion by Adipocytes. Exp Clin Endocrinol Diabetes 2008.

9. Nakagawa Y, Kishida K, Kihara S, Sonoda M, Hirata A, Yasui A, Nishizawa H, Nakamura T, Yoshida R, Shimomura I, Funahashi T. Nocturnal reduction in circulating adiponectin concentrations related to hypoxic stress in severe obstructive sleep apnea-hypopnea syndrome. Am J Physiol Endocrinol Metab 294:E778-84, 2008.

10. Han F. Obstructive sleep apnea hypopnea syndrome: a proinflammatory disorder. Chin Med J (Engl) 120:1475-6, 2007.

11. Harsch I A, Bergmann T, Koebnick C, Wiedmann R, Ruderich F, Hahn E G, Konturek P C. Adiponectin, resistin and subclinical inflammation—the metabolic burden in Launois Bensaude Syndrome, a rare form of obesity. J Physiol Pharmacol 58 Suppl 1:65-76, 2007.

12. Alam I, Lewis K, Stephens J W, Baxter J N. Obesity, metabolic syndrome and sleep apnoea: all pro-inflammatory states. Obes Rev 8:119-27, 2007.

13. Sharma S K, Kumpawat S, Goel A, Banga A, Ramakrishnan L, Chaturvedi P. Obesity, and not obstructive sleep apnea, is responsible for metabolic abnormalities in a cohort with sleep-disordered breathing. Sleep Med 8:12-7, 2007.

14. Masserini B, Morpurgo P S, Donadio F, Baldessari C, Bossi R, Beck-Peccoz P, Orsi E. Reduced levels of adiponectin in sleep apnea syndrome. J Endocrinol Invest 29:700-5, 2006.

15. Makino S, Handa H, Suzukawa K, Fujiwara M, Nakamura M, Muraoka S, Takasago I, Tanaka Y, Hashimoto K, Sugimoto T. Obstructive sleep apnoea syndrome, plasma adiponectin levels, and insulin resistance. Clin Endocrinol (Oxf) 64:12-9, 2006.

16. Wolk R, Svatikova A, Nelson C A, Gami A S, Govender K, Winnicki M, Somers V K. Plasma levels of adiponectin, a novel adipocyte-derived hormone, in sleep apnea. Obes Res 13:186-90, 2005.

17. Zhang X L, Yin K S, Mao H, Wang H, Yang Y. Serum adiponectin level in patients with obstructive sleep apnea hypopnea syndrome. Chin Med J (Engl) 117:1603-6, 2004.

18. Zhang X L, Huang Q S, Huang M, Yin K S. [Serum adiponectin levels in patients with obstructive sleep apnea-hypopnea syndrome]. Zhonghua Jie He He Hu Xi Za Zhi 27:515-8, 2004.

19. Morgenthaler T I, Kagramanov V, Hanak V, Decker P A. Complex sleep apnea syndrome: is it a unique clinical syndrome? Sleep 29:1203-9, 2006.

20. Thakkar K, Yao M. Diagnostic studies in obstructive sleep apnea. Otolaryngol Clin North Am 40:785-805, 2007.

21. Lowe A A, Gionhaku N, Takeuchi K, Fleetham J A. Three-dimensional CT reconstructions of tongue and airway in adult subjects with obstructive sleep apnea. Am J Orthod Dentofacial Orthop 90:364-74, 1986.

22. Galvin J R, Rooholamini S A, Stanford W. Obstructive sleep apnea: diagnosis with ultrafast CT. Radiology 171:775-8, 1989.

23. Stauffer J L, Zwillich C W, Cadieux R J, Bixler E O, Kales A, Varano L A, White D P. Pharyngeal size and resistance in obstructive sleep apnea. Am Rev Respir Dis 136:623-7, 1987.

24. Avrahami E, Solomonovich A, Englender M. Axial CT measurements of the cross-sectional area of the oropharynx in adults with obstructive sleep apnea syndrome. AJNR Am J Neuroradiol 17:1107-11, 1996.

25. Avrahami E, Englender M. Relation between CT axial cross-sectional area of the oropharynx and obstructive sleep apnea syndrome in adults. AJNR Am J Neuroradiol 16:135-40, 1995.

26. Shepard J W Jr, Garrison M, Vas W. Upper airway distensibility and collapsibility in patients with obstructive sleep apnea. Chest 98:84-91, 1990.

27. Isono S, Feroah T R, Hajduk E A, Brant R, Whitelaw W A, Remmers J E. Interaction of cross-sectional area, driving pressure, and airflow of passive velopharynx. J Appl Physiol 83:851-9, 1997.

28. Haponik E F, Smith P L, Bohlman M E, Allen R P, Goldman S M, Bleecker E R. Computerized tomography in obstructive sleep apnea. Correlation of airway size with physiology during sleep and wakefulness. Am Rev Respir Dis 127:221-6, 1983.

29. Caballero P, Alvarez-Sala R, Garcia-Rio F, Prados C, Hernan M A, Villamor J, Alvarez-Sala J L. CT in the evaluation of the upper airway in healthy subjects and in patients with obstructive sleep apnea syndrome. Chest 113:111-6, 1998.

30. Yucel A, Unlu M, Haktanir A, Acar M, Fidan F. Evaluation of the upper airway cross-sectional area changes in different degrees of severity of obstructive sleep apnea syndrome: cephalometric and dynamic CT study. AJNR Am J Neuroradiol 26:2624-9, 2005.

31. Vos W, De Backer J, Devolder A, Vanderveken O, Verhulst S, Salgado R, Germonpre P, Partoens B, Wuyts F, Parizel P, De Backer W. Correlation between severity of sleep apnea and upper airway morphology based on advanced anatomical and functional imaging. J Biomech 40:2207-13, 2007.

32. Miki H, Hida W, Kikuchi Y, Takishima T. Effect of sleep position on obstructive sleep apnea. Tohoku J Exp Med 156 Suppl:143-9, 1988.

33. Phillips B A, Okeson J, Paesani D, Gilmore R. Effect of sleep position on sleep apnea and parafunctional activity. Chest 90:424-9, 1986.

34. Cartwright R D, Lloyd S, Lilie J, Kravitz H. Sleep position training as treatment for sleep apnea syndrome: a preliminary study. Sleep 8:87-94, 1985.

35. Cartwright R D. Effect of sleep position on sleep apnea severity. Sleep 7:110-4, 1984.

36. Shepard J W Jr, Thawley S E. Localization of upper airway collapse during sleep in patients with obstructive sleep apnea. Am Rev Respir Dis 141:1350-5, 1990.

37. Neill A M, Angus S M, Sajkov D, McEvoy R D. Effects of sleep posture on upper airway stability in patients with obstructive sleep apnea. Am J Respir Crit. Care Med 155:199-204, 1997.

38. Puhan M A, Suarez A, Lo Cascio C, Zahn A, Heitz M, Braendli O. Didgeridoo playing as alternative treatment for obstructive sleep apnoea syndrome: randomised controlled trial. BMJ 332:266-70, 2006.

39. Sullivan C E, Issa F G, Berthon-Jones M, McCauley V B, Costas L J. Home treatment of obstructive sleep apnoea with continuous positive airway pressure applied through a nose-mask. Bull Eur Physiopathol Respir 20:49-54, 1984.

40. Sullivan C E, Berthon-Jones M, Issa F G. Nocturnal nasal-airway pressure for sleep apnea. N Engl J Med 309:112, 1983.

41. Sullivan C E, Berthon-Jones M, Issa F G. Remission of severe obesity-hypoventilation syndrome after short-term treatment during sleep with nasal continuous positive airway pressure. Am Rev Respir Dis 128:177-81, 1983.

42. Sullivan C E, Issa F G, Berthon-Jones M, Eves L. Reversal of obstructive sleep apnea by continuous positive airway pressure applied through the nares. Lancet 1:862-5, 1981.

43. Kuhlo W, Doll E, Franck M C. [Successful management of Pickwickian syndrome using long-term tracheostomy]. Dtsch Med Wochenschr 94:1286-90, 1969.

We claim:

1. A nasal-pharyngeal bypass useful for establishing an airway for the patient, the bypass comprising:
   a collapsible tube having a proximal end, a distal end, a lumen extending through the tube, and a length between the proximal and distal ends so that, when the tube is inserted through the patient's nostril, through the patient's nasal cavity, and into the patient's throat, the distal end of the tube is above the patient's epiglottis and the proximal end of the tube is outside of the patient's nostril;
   wherein the tube has a collapsed configuration in which the tube is sized to be inserted through the patient's nasal cavity; and
   wherein the tube has an expanded configuration in which the tube is sized to be retained in the patient's nasal cavity and establish a bypass airway for the patient through the lumen of the tube;

wherein the tube comprises a flat sheet, the flat sheet having a cavity therein, a closed distal end, and an opening in the proximal end communicating with the cavity, wherein the cavity extends from the distal end to the proximal end, wherein the flat sheet is rolled onto itself to form the tube, and including a one-way valve in the proximal opening; and wherein the proximal and distal ends define a longitudinal direction, and wherein the cavity includes finger portions which extend away from the longitudinal direction.

2. A nasal-pharyngeal bypass according to claim 1, wherein the tube comprises a coil spring and a coating around the coil spring.

3. A nasal-pharyngeal bypass according to claim 2, wherein the coil spring collapsed configuration has a V-shaped cross-section.

4. A nasal-pharyngeal bypass according to claim 2, further comprising a mandrel extending through the coil spring in the collapsed configuration, the mandrel including an end piece sized so that, when the mandrel is pulled proximally out of the collapsed tube, the end piece expands the coil spring into the expanded configuration.

5. A nasal-pharyngeal bypass according to claim 1, wherein the flat sheet comprises a side edge, and wherein the side edge is not connected to other portions of the sheet when the sheet is rolled onto itself to form the tube.

6. A nasal-pharyngeal bypass according to claim 1, further comprising:
a mandrel extending proximally from the distal end.

7. A nasal-pharyngeal bypass according to claim 6, wherein the mandrel is embedded in the sheet adjacent to the cavity.

8. A nasal-pharyngeal bypass according to claim 6, further comprising:
a lumen extending through the sheet from the distal to the proximal end; and
wherein the mandrel is movably positioned in the sheet lumen adjacent to the cavity.

9. A nasal-pharyngeal bypass according to claim 6, wherein the mandrel is formed of a malleable material.

10. A nasal-pharyngeal bypass according to claim 6, wherein the mandrel comprises a bend along its length.

11. A nasal-pharyngeal bypass according to claim 6, wherein the mandrel comprises an enlarged distal tip.

12. A nasal-pharyngeal bypass according to claim 1, wherein the one-way valve comprises a reed valve, and further comprising an inflation tube sized to be received in the reed valve.

13. A nasal-pharyngeal bypass according to claim 1, wherein the flat sheet comprises at least a portion formed of a permeable material.

* * * * *